United States Patent [19]

Hughes et al.

[11] 4,033,940

[45] July 5, 1977

[54] CYCLIZATION OF PEPTIDES

[75] Inventors: John L. Hughes, Kankakee; Jay K. Seyler, Bourbonnais; Robert C. Liu, Kankakee, all of Ill.

[73] Assignee: Armour Pharmaceutical Company, Phoenix, Ariz.

[22] Filed: Nov. 12, 1975

[21] Appl. No.: 631,408

[52] U.S. Cl. .................. 260/112.5 S; 260/112.5 R
[51] Int. Cl.² ....................................... C07C 103/52
[58] Field of Search ............... 260/112.5 R, 112.5 S

[56] References Cited

UNITED STATES PATENTS 3,929,758   12/1975   Hughes et al. ............. 260/112.5 R

OTHER PUBLICATIONS

Hiskey et al.: J. Org. Chem., 35, 1118–1121 (1970).

*Primary Examiner*—Delbert R. Phillips
*Attorney, Agent, or Firm*—Richard R. Mybeck; Frank T. Barber; Carl C. Batz

[57] ABSTRACT

The synthesis of a disulfide cyclic peptide by preparing an intermediate peptide containing an amino terminal cystine residue and a cysteine residue located in a position within the amino acid sequence, to give a desired peptide, and placing such intermediate peptide in a solution substantially free of oxygen at a pH of from about 5 to 10 until rearrangement takes place to yield a cyclic disulfide peptide and to displace a molecule of cysteine from the amino terminal cysteine residue. The disclosure also embraces said intermediate peptides as new compounds and the processes by which they are prepared.

21 Claims, No Drawings

CYCLIZATION OF PEPTIDES

This invention pertains to cyclization of peptides and more particularly to methods for treating peptides containing a cysteine residue within the amino acid sequence and a cystine residue at the amino terminal end to produce a disulfide bond between such residues and so form a ring structure. Such methods are useful in the synthesis of peptides which have biological activity and other such naturally occurring peptides may vary depending upon the species from which they are obtained, all such peptides which were originally obtained from natural sources, such as by extraction from the glands of humans, domestic animals, fishes, frogs, or reptiles, contain the ring structure referred to above. The amino acid sequence of some known biologically active peptides containing cysteine groups joined by disulfide bonds in a ring structure are given in Table I.

TABLE I

Typical Peptides Containing Cysteine Ring Structures

Oxytocin: H—CYS—TYR—ILE—GLN—ASN—CYS—PRO—LEU—GLY—NH₂
(disulfide bond between the two CYS residues)

Vasopressin: H—CYS—TYR—PHE—GLN—ASN—CYS—PRO—ARG—GLY—NH₂
(disulfide bond between the two CYS residues)

Salmon Calcitonin: H—CYS—SER—ASN—LEU—SER—THR—CYS—VAL—LEU—GLY—
LYS—LEU—SER—GLN—GLU—LEU—HIS—LYS—LEU—GLN—THR—
TYR—PRO—ARG—THR—ASN—THR—GLY—SER—GLY—THR—PRO—NH₂

Human Calcitonin: H—CYS—GLY—ASN—LEU—SER—THR—CYS—MET—LEU—GLY—THR—
TYR—THR—GLN—ASP—PHE—ASN—LYS—PHE—HIS—THR—PHE—
PRO—GLN—THR—ALA—ILE—GLY—VAL—GLY—ALA—PRO—NH₂

Porcine Calcitonin: H—CYS—SER—ASN—LEU—SER—THR—CYS—VAL—LEU—SER—
ALA—TYR—TRP—ARG—ASN—LEU—ASN—ASN—PHE—HIS—ARG—
PHE—SER—GLY—MET—GLY—PHE—GLY—PRO—GLU—THR—PRO—NH₂

Bovine Calcitonin: H—CYS—SER—ASN—LEU—SER—THR—CYS—VAL—LEU—SER—ALA—
TYR—TRP—LYS—ASP—LEU—ASN—ASN—TYR—HIS—ARG—PHE—
SER—GLY—MET—GLY—PHE—GLY—PRO—GLU—THR—PRO—NH₂ which are useful in the treatment of certain diseases in animals and man.

The invention pertains also to intermediate peptides which are precursors of cyclic disulfide peptides and to the preparation of such intermediate peptides.

BACKGROUND

Many peptides are known which are biologically active and are useful in the treatment of diseases and which contain a disulfide ring. Calcitonins, which are useful in the treatment of Paget's disease, contain a ring structure involving cysteine groups at the 1st and 7th positions in their amino acid chains. Oxytocin is useful for the therapeutic induction or stimulation of labor in humans and animals and also to control pastpartum uterine bleeding. It contains a disulfide ring structure between the cysteine groups at positions 1 and 6 in its amino acid chain. Vasopressin and its analog lypressin are used as antidiuretic drugs in man and contain disulfide ring structures between the cysteine groups at positions 1 and 6 in their amino acid sequences (handbood of Biochemistry, pages C-164 to C-188).

Although the kind and sequence of the amino acid groups for the calcitonins, oxytocin, vasopressin, and In prior attempts by others to prepare synthetically a peptide such as those referred to in Table I, the only method available for producing a closed disulfide ring structure was to attempt to form the intermediate peptide having the desired amino acid chain and then subject this peptide to an oxidative process using oxidizing agents, to form the disulfide bond between the two cysteine residues. Such oxidative methods have been described in the literture (Katsoyannis, P.G., The Chemistry of Polypeptides, Plenum Press, 1974, pages 60–85). A main disadvantage of these processes is the exposure of the highly labile peptide molecule to oxidizing agents. This treatment can cause inactivation of the peptide resulting in a lower yield of biologically active products.

The art has long needed satisfactory processes for the formation of the disulfide bond between the cysteine moieties of a peptide which do not require the use of oxidizing agents. Accordingly, we have set ourselves to the discovery of practical and efficient methods for the formation of a cyclic disulfide bond between the cysteine moieties of a peptide.

SUMMARY

We discovered a method for forming this bond between the cysteine moieties and this method is disclosed in our copending patent application Ser. No. 505,344 filed Sept. 12, 1974. We have now discovered another method for forming such bond between a cysteine residue within the amino acid sequence and a cysteine residue at the terminal end of the amino acid chain. This process also avoids the use of oxidative conditions. It involves the provision of a peptide in which the cysteine residue at the amino terminal end of the peptide has its thiol function protected by being bonded through a disulfide bond to a second cysteine gruop. The combination of two cysteine groups bonded by a disulfide bond is the amino acid cystine. The disulfide bond of cystine is stable to the subsequent acid cleavage conditions commonly used in peptide synthesis, i.e., liquid hydrogen fluoride or hydrogen bromide in acetic acid. The second cysteine residue of the peptide, located in any other position as required to give the desired sequence, has its thiol function protected by an acid cleavage labile group such as a tertiary butylthio group or a benzyl group or its like derivatives. The resulting intermediate peptide obtained after the subsequent cleavage step contains a cystine moiety at its amino terminal end and a free thiol function at the second cysteine residue located in any other position to give a desired amino acid sequence. This intermediate peptide may be held in oxygen-free solution until spontaneous rearrangement takes place completing the desired disulfide ring between the two cysteine moieties with displacement of one-half of the cystine residue or the cysteine protecting group from the cysteine residue at the amino terminal end of the intermediate peptide. The total process thus produces the desired cyclic disulfide peptide by a simple mild rearrangement procedure that does not involve the use of oxidizing reagents or conditions.

DESCRIPTION OF INVENTION

Our present process is applicable to the synthesis of any cyclic disulfide peptide wherein the disulfide bond is between two cysteine residues in the amino acid chain with one of these cysteine residues located at the amino terminal end of the peptide. The process is particularly advantageous in the synthesis of labile biologically active peptides because the disulfide bond formation is performed under conditions which avoid oxidation and to not otherwise disturb the peptide structure.

We may start with the preparation of an intermediate peptide and build the amino acid chain of the oxytocin, calcitonin, or any other such peptide containing two cysteine residues. The amino acid chain may be assembled by application of classical synthesis techniques or the new solid phase techniques (Merrifield, R. B. *Advances in Enzymology* Interscience, New York, 1969, Chapter 32, 221-296 and Stewart, J. and Young, J. *Solid Phase Peptide Synthesis*, W. H. Freeman & Co., San Francisco, 1969).

We prefer to use the solid phase type of synthesis. In this synthesis the amino acids are added one at a time to the resin until the total peptide sequence has been built up on the resin. The functional groups of the amino acids are protected by blocking groups. The α-amino group of the amino acids is protected by a tertiary butyloxycarbonyl group we designate as BOC. The hydroxyl functions of serine and threonine are protected by a benzyl or benzyl derivative group such as 4-methoxybenzyl, 4-methybenzyl, 3,4-dimethylbenzyl, 4-chlorobenzyl, 2,6-dichlorobenzyl, 4-nitrobenzyl, benzhydryl, or an equivalent thereof. We use the term BZ to represent benzyl or benzyl derivative groups. The hydroxyl function of tyrosine may be unprotected, may be protected by a benzyl or benzyl derivative group as described above, as a BZ group, or may be protected by a benzyloxycarbonyl or a benzyloxycarbonyl derivative such as 2-chlorobenzyloxycarbonyl or a 2-bromobenzyloxycarbonyl group or equivalent thereof. We use the term W to represent either no protective group, a BZ group, a benzyloxycarbonyl group or a benzyloxycarbonyl derivative group. The guanidino function of arginine may be protected by a nitro group, a tosyl group or an equivalent thereof. We use the character T to represent either a nitro group or a tosyl group. The ε-amino function of lysine may be proteced by a benzyloxycarbonyl group or a benzyloxycarbonyl derivative such as 2-chlorobenzyloxycarbonyl, 2-bromobenzyloxycarbonyl, 3,4-dimethylbenzyloxycarbonyl or the equivalent thereof. We use the character V to represent a benzyloxycarbonyl group or a benxyloxycarbonyl derivative group. The protective groups used on the imidazole nitrogen of histidine are the benzyloxycarbonyl group and benzyloxycarbonyl derivatives such as described above for lysine and are designated V. The ω-carboxylic acid groups of glutamic and aspartic acids are protected by a benzyl or benzyl derivative group such as described for the protection of the hydroxyl function of serine and threonine. These protective groups are representated by the character BZ.. The acid labile protecting group for the thiol function of cysteine is designated as P. The term acid labile protecting group is used here as those groups that are cleaved by strong acids such as liquid hydrogen fluoride or other halogen acids in acetic or trifluoroacetic acids. The character P is then used to represent acid labile groups such as the tertiary butylthio group, the isopropylthio group, the benzyl group or benzyl derivative groups such as 4-methoxybenzyl, 4-methylbenzyl, 3,4-dimethylbenzyl, 4-chlorobenzyl, 2,6-dichlorobenzyl, 4-nitrobenzyl, benzyhdryl or an equivalent thereof.

The disulfide peptides to which our improved process is applicable have at least two cysteine residues with one of the residues located at the amino terminal end of the amino acid sequence. The disulfide cyclic peptides are obtained in three steps. In the first step an intermediate peptide is produced with functional groups protected by acid labile groups except for the thiol group of the cysteine residue at the amino terminal end of the peptide. For this residue, a cystine group is used which is equivalent to using a cysteine residue with its thiol function protected by disulfide bond formation with another cysteine group. The other cysteine residue in the amino acid sequence of the desired peptide has its thiol function protected by an acid labile protecting group such as a benzyl group or its like derivative. The second step of the process is acid treatment of the intermediate peptide to remove all protecting groups from the peptide except the acid stable disulfide protecting group which is contained in the cystine residue at the amino terminal end of the peptide. The other cysteine residue in the desired peptide sequence now has a free thiol group. Its acid labile protecting group was removed by the acid cleavage step. The third step in the process is the formation of the desired disulfide bond between the two cysteine residues of the sequence. This step takes place by a spontaneous rearrangement in an oxygen-free media with the displacement of the cysteine from the amino terminal cystine residue.

The three steps of the process are shown below schematically.

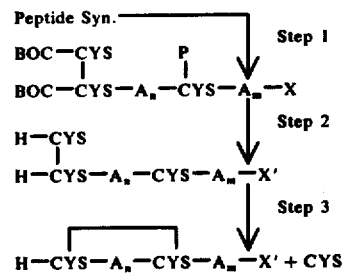

Where BOC = α-tertiary butyloxy-carbonyl
A = amino acid chain
X = NH$_2$, OH or a solid phase resin support
X' = OH or NH$_2$
P = Acid labile protecting group
n and m are equal to zero or an integer to give a desired peptide sequence According to the solid phase technology, the amino acid in the highest numbered position in the chain of the peptide to be synthesized is coupled to the resin using the protective groups as above referred to followed by removal of the BOC protective group of the α-amino group; then the next amino acid of the next highest position is coupled to the amino acid group last added using appropriate protective groups, etc. until the desired chain of amino acids is completed. Suitable combinations of amino acid groups and protective groups may be obtained and these combinations reacted with the peptide previously formed to add the successive amino acid groups. Such protected amino acids may be obtained commercially from chemical supply houses.

To illstrate the synthesis of amino acid chains occurring in typical peptides to which our process is applicable, we give in Tables II to VII some typical reactants (which contain the amino acid group and protecting groups) for use in the synthesis of typical amino acid chain sequences.

TABLE II

| Position Number | Typical Reactants for Use in the Synthesis of Oxytocin Amino Acid Reactant |
|---|---|
| 9 | BOC-glycine |
| 8 | BOC-L-leucine |
| 7 | BOC-L-proline |
| 6 | BOC-S-p-methoxybenzyl-L-cysteine, BOC-S-benzyl-L-cysteine, BOC-S-3,4-dimethylbenzyl-L-cysteine, BOC-S-isopropylthio-L-cysteine, or BOC-S-tertiary-butylthio-L-cysteine |
| 5 | BOC-L-asparagine p-nitrophenyl ester |
| 4 | BOC-L-glutamine p-nitrophenol ester |
| 3 | BOC-L-isoleucine |
| 2 | BOC-O-benzyl-L-tyrosine, BOC-L-tyrosine, or BOC-O-2-bromo-benzyloxycarbonyl-L-tyrosine |
| 1 | Bis-BOC-L-cystine |

TABLE III

| Position Number | Typical Reactants For Use In The Synthesis Of Salmon Calcitonin Amino Acid Reactant |
|---|---|
| 32 | BOC-L-proline |
| 31 | BOC-O-benzyl-L-threonine |
| 30 | BOC-glycine |
| 29 | BOC-O-benzyl-L-serine |
| 28 | BOC-glycine |
| 27 | BOC-O-benzyl-L-threonine |
| 27 | BOC-O-benzyl-L-threonine |
| 26 | BOC-L-asparagine p-nitrophenyl ester |
| 25 | BOC-O-benzyl-L-threonine |
| 24 | BOC-ω-nitro-L-arginine or BOC-ω-tosyl-L-arginine |
| 23 | BOC-L-proline |
| 22 | BOC-O-benzyl-L-tyrosine, BOC-L-tyrosine, or BOC-O-2-bromo-benzyloxycarbonyl-L-tyrosine |
| 21 | BOC-O-benzyl-L-threonine |
| 20 | BOC-L-glutamine p-nitrophenyl ester |
| 19 | BOC-L-leucine |
| 18 | BOC-ε-CBZ-L-lysine or BOC-ε-2-chlorobenzyloxycarbonyl-L-lysine |
| 17 | BOC-N(im)-CBZ-L-histidine |
| 16 | BOC-L-leucine |
| 15 | BOC-L-glutamic acid γ-benzyl ester |
| 14 | BOC-L-glutamine p-nitrophenyl ester |
| 13 | BOC-L-benzyl-L-serine |
| 12 | BOC-L-leucine |
| 11 | BOC-ε-CBZ-L-lysine or BOC-ε-2-chlorobenzyloxycarbonyl-L-lysine |
| 10 | BOC-glycine |
| 9 | BOC-L-leucine |
| 8 | BOC-L-valine |
| 7 | BOC-S-p-methoxybenzyl-L-cysteine, BOC-S-benzyl-L-cysteine, BOC-s-3,4-dimethylbenzyl-L-cysteine, BOC-S-isopropylthio-L-cysteine, or BOC-S-tertiary-butylthio-L-cysteine |
| 6 | BOC-O-benzyl-L-threonine |
| 5 | BOC-O-benzyl-L-serine |
| 4 | BOC-L-leucine |
| 3 | BOC-L-asparagine p-nitrophenyl ester |
| 2 | BOC-O-benzyl-L-serine |
| 1 | Bis-BOC-L-cystine |

TABLE IV

| Position Number | Typical Reactants for Use in the Synthesis of Human Calcitonin Amino Acid Reactant |
|---|---|
| 32 | BOC-L-proline |
| 31 | BOC-L-alanine |
| 30 | BOC-glycine |
| 29 | BOC-L-valine |
| 28 | BOC-glycine |
| 27 | BOC-L-isoleucine |
| 26 | BOC-L-alanine |
| 25 | BOC-O-benzyl-L-threonine |
| 24 | BOC-L-glutamine p-nitrophenyl ester |
| 23 | BOC-L-proline |
| 22 | BOC-L-phenylalanine |
| 21 | BOC-O-benzyl-L-threonine |
| 20 | BOC-N(im)-CBZ-L-histidine |
| 19 | BOC-L-phenylalanine |
| 18 | BOC-εCBZ-L-lysine or BOC-ε-2-chlorobenzyloxycarbonyl-L-lysine |
| 17 | BOC-L-asparagine p-nitrophenyl ester |
| 16 | BOC-L-phenylalanine |
| 15 | BOC-L-aspartic acid γ-benzyl ester |
| 14 | BOC-L-glutamine p-nitrophenyl ester |
| 13 | BOC-O-benzyl-L-theonine |
| 12 | BOC-O-benzyl-L-tyrosine, BOC-L-tyrosine, or BOC-O-2-bromo-benzyloxycarbonyl-L-tyrosine |
| 11 | BOC-O-benzyl-L-threonine |
| 10 | BOC-glycine |
| 9 | BOC-L-leucine |
| 8 | BOC-L-methionine |
| 7 | BOC-S-p-methoxybenzyl-L-cysteine, BOC-S-benzyl-L-cysteine, BOC-S-3,4-dimethylbenzyl-L-cysteine, BOC-S-isopropylthio-L-cysteine, or BOC-S-tertiary-butylthio-L-cysteine |
| 6 | BOC-O-benzyl-L-threonine |
| 5 | BOC-O-benzyl-L-serine |
| 4 | BOC-L-leucine |

TABLE IV-continued

Typical Reactants for Use in the Synthesis of Human Calcitonin

| Position Number | Amino Acid Reactant |
|---|---|
| 3 | BOC-L-asparagine p-nitrophenyl ester |
| 2 | BOC-glycine |
| 1 | Bis-BOC-L-cystine |

TABLE V

Typical Reactants for Use in the Synthesis of Vasopressin

| Position Number | Amino Acid Reactant |
|---|---|
| 9 | BOC-glycine |
| 8 | BOC-ω-tosyl-L-arginine or BOC-ω-nitro-L-arginine |
| 7 | BOC-L-proline |
| 6 | BOC-S-p-methoxybenzyl-L-cysteine, BOC-S-benzyl-L-cysteine, BOC-S-3,4 dimethylbenzyl-L-cysteine, BOC-S-isopropylthio-L-cysteine, or BOC-S-tertiary-butylthio-L-cysteine |
| 5 | BOC-L-asparagine p-nitrophenyl ester |
| 4 | BOC-L-glutamine p-nitrophenyl ester |
| 3 | BOC-L-phenylalanine |
| 2 | BOC-O-benzyl-L-tyrosine, BOC-L-tyrosine, or BOC-O-2-bromobenzyloxycarbonyl-L-tyrosine |
| 1 | Bis-BOC-L-cystine |

TABLE VI

Typical Reactants for Use in the Synthesis of Porcine Calcitonin

| Position Number | Amino Acid Reactant |
|---|---|
| 32 | BOC-L-proline |
| 31 | BOC-O-benzyl-L-threonine |
| 30 | BOC-L-glutamic acid γ-benzyl ester |
| 29 | BOC-L-proline |
| 28 | BOC-glycine |
| 27 | BOC-L-phenylalanine |
| 26 | BOC-glycine |
| 25 | BOC-L-methionine |
| 24 | BOC-glycine |
| 23 | BOC-O-benzyl-L-serine |
| 22 | BOC-L-phenylalanine |
| 21 | BOC-ω-tosyl-L-arginine or BOC-ω-nitro-L-arginine |
| 20 | BOC-N(im)-CBZ-L-histidine |
| 19 | BOC-L-phenylalanine |
| 18 | BOC-L-asparagine p-nitrophenyl ester |
| 17 | BOC-L-asparagine p-nitrophenyl ester |
| 16 | BOC-L-leucine |
| 15 | BOC-L-asparagine p-nitrophenyl ester |
| 14 | BOC-ω-tosyl-L-arginine or BOC-ω-nitro-L-arginine |
| 13 | BOC-L-tryptophan |
| 12 | BOC-O-benzyl-L-tyrosine, BOC-L-tyrosine, or BOC-2-bromobenzyloxycarbonyl-L-tyrosine |
| 11 | BOC-L-alanine |
| 10 | BOC-O-benzyl-L-serine |
| 9 | BOC-L-leucine |
| 8 | BOC-L-valine |
| 7 | BOC-S-p-methoxybenzyl-L-cysteine, BOC-S-benzyl-L-cysteine, BOC-S-3,4-dimethylbenzyl-L-cysteine, BOC-S-isopropylthio-L-cysteine, or BOC-tertiary-butylthio-L-cysteine |
| 6 | BOC-O-benzyl-L-threonine |
| 5 | BOC-O-benzyl-L-serine |
| 4 | BOC-L-leucine |
| 3 | BOC-L-asparagine p-nitrophenyl ester |
| 2 | BOC-O-benzyl-L-serine |
| 1 | Bis-BOC-L-cystine |

TABLE VII

Typical Reactants for Use in the Synthesis of Bovine Calcitonin

| Position Number | Amino Acid Reactant |
|---|---|
| 32 | BOC-L-proline |
| 31 | BOC-O-benzyl-L-threonine |
| 30 | BOC-L-glutamic acid γ-benzyl ester |
| 29 | BOC-L-proline |
| 28 | BOC-glycine |
| 27 | BOC-L-phenylalanine |
| 26 | BOC-glycine |
| 25 | BOC-L-methionine |
| 24 | BOC-glycine |
| 23 | BOC-O-benzyl-L-serine |
| 22 | BOC-L-phenylalanine |
| 21 | BOC-ω-tosyl-L-arginine or BOC-ω-nitro-L-arginine |
| 20 | BOC-N(im)-CBZ-L-histidine |
| 19 | BOC-O-benzyl-L-tyrosine, BOC-L-tyrosine or BOC-O-2-bromobenzyloxycarbonyl-L-tyrosine |
| 18 | BOC-L-asparagine p-nitrophenyl ester |
| 17 | BOC-L-asparagine p-nitrophenyl ester |
| 16 | BOC-L-leucine |
| 15 | BOC-L-aspartic acid γ-benzyl ester |
| 14 | BOC-ε-CBZ-L-lysine or BOC-ε-2-chlorobenzyloxycarbonyl-L-lysine |
| 13 | BOC-L-tryptophan |
| 12 | BOC-O-benzyl-L-tyrosine, BOC-L-tyrosine, or BOC-O-2-bromobenzyloxycarbonyl-L-tyrosine |
| 11 | BOC-L-alanine |
| 10 | BOC-O-benzyl-L-serine |
| 9 | BOC-L-leucine |
| 8 | BOC-L-valine |
| 7 | BOC-S-p-methoxybenzyl-L-cysteine, BOC-S-benzyl-L-cysteine, BOC-S-3,4-dimethylbenzyl-L-cysteine, BOC-S-isopropylthio-L-cysteine, or BOC-tertiary-butylthio-L-cysteine |
| 6 | BOC-O-benzyl-L-threonine |
| 5 | BOC-O-benzyl-L-serine |
| 4 | BOC-L-leucine |
| 3 | BOC-L-asparagine p-nitrophenyl ester |
| 2 | BOC-O-benzyl-L-serine |
| 1 | Bis-BOC-L-cystine |

The peptides containing an amino terminal cysteine residue and a free cysteine residue at another position in the sequence which we prepare as intermediates in our process are characterized before acid cleavage by their containing the following structure:

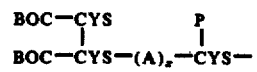

and after acid treatment to cleave the acid labile protective groups, by the structure:

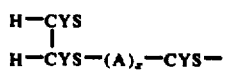

where
A is an amino acid residue
X is zero or a whole integer
CYS is a cysteine residue
P is a tertiary or a secondary alkylthio group or a benzyl or benzyl derivative group.

The cleaved peptide thus has one cysteine residue with a free sulfhydryl function, the other cysteine residue having its sulfhydryl function participating in a disulfide bond with another cysteine residue. This combination of two cysteine residues linked by a disulfide bond is termed a cystine residue. It will be seen that the peptides produced as a result of reactions in each of Tables II to VII may each be so characterized.

Any peptide which may be characterized as above indicated may be used as an intermediate in our process and subjected to our ring closing procedure. Any such peptide containing a structure having a cysteine residue which has a free sulfhydryl function and a cystine residue at the amino terminal end may be held in solution (any solution in which it is soluble), with aqueous or alcoholic solutions preferred, at a pH of from about 5 to 10 until it undergoes spontaneous rearrangement to the desired cyclic disulfide cysteine peptide with the displacement of a molecule of cysteine.

The rearrangement reaction is facilitated by adjusting the pH of the solution to from 5.0 to 8.5, preferably from 6.0 to 8.5, and best at about 7.5 as by the addition of ammonium or alkali hydroxides. A pH below 6.0 may be used, but the rearrangement proceeds more slowly than is desirable, and a pH up to about 10.0 or 10.5 can be used, but when a pH higher than about 8.5 is used there is some danger of loss in yield.

Further we prefer to agitate the solution during the period of the rearrangement reaction which may take from about 1 to 48 hours, but usually is complete in about 24 hours. The reaction is facilitated by stirring or other form of agitation. This treatment may be continued for still longer periods of time without harm to the product.

Also, we take care to avoid the presence of oxygen or oxidizing substances, and keep the solution substantially free of oxygen. We prefer to place the solution containing the peptide under a stream of an inert gas such as nitrogen.

The intermediate peptide which contains the structure

```
H—CYS
    |
H—CYS—(A)ₓ—CYS—
``` in which the internal CYS group has a free sulfhydryl function and the amino terminal end has a cystine residue, is by our ring closing procedure converted to a peptide in which such structure becomes

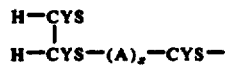

where

CYS is a cysteine residue
A is an amino acid resiude and
X is zero or a whole integer.

If the procedure has been carefully carried out according to the procedures and precautions above outlined, the ring closing procedure produces no other changes in the peptide other than rearrangement to form a disulfide bond between two cysteines and displace a molecule of cysteine.

The peptide solution obtained by our ring closing procedure as above set forth may be purified by procedures known to this art. The solution may be subjected to a combination of gel-filtration procedures and ion-exchange chromatography methods. The final purified product may be obtained from solution by freeze-drying. The resulting peptide will be found to be chemically and biologically equivalent to such peptide which has been obtained from natural sources.

One application of our improved process is in the synthesis of salmon calcitonin. As set forth in Example I, proline maybe coupled to the resin using the reactant BOC-L-proline at position 32, then threonine maybe coupled using the reactant BOC-O-benzyl-L-threonine at position No. 31, the coupling being continued using in sequence the reactants set forth in Table III herein. When position No. 7 is reached, a cysteine derivative containing an acid labile sulfur protecting group may be used; and when position No. 1 is reached, bis-BOC-L-cystine may be used as the cysteine derivative. Upon the completion of the desired amino acid chain, the resin peptide may be treated with hydrogen fluoride to remove the resin and all of the remaining acid labile protective groups. The solution resulting from the acid cleavage step may be diluted with water and adjusted to a pH of about 7.5 by the addition of ammonium hydroxide. The solution may then be agitated under a stream of nitrogen gas for 3 to 48 hours. Upon purification of the resulting product, it should be chemically and biologically equivalent to natural salmon calcitonin.

The formula of the peptide resulting from the reactions referred to in Table III, and before cleavage of the resin may be written;

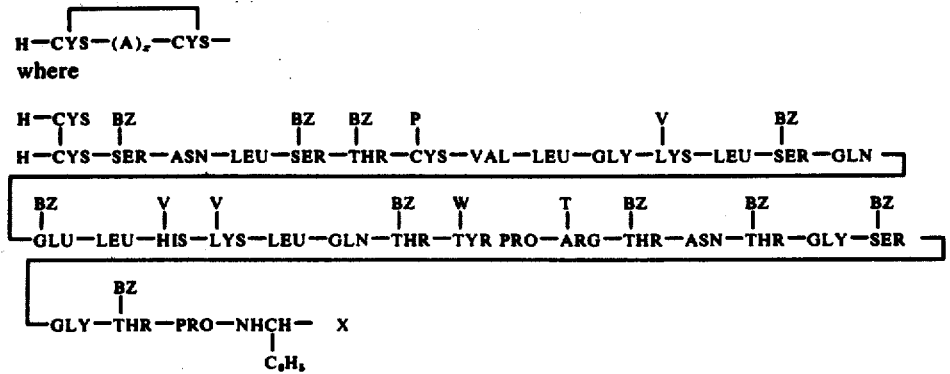

The formula of this peptide obtained upon anhydrous halogen acid cleavage becomes:

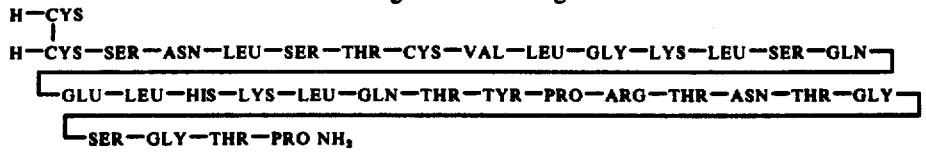

which is precursor of salmon calcitonin.

After subjecting this peptide to our improved cyclizing method as herein described, the peptide becomes:

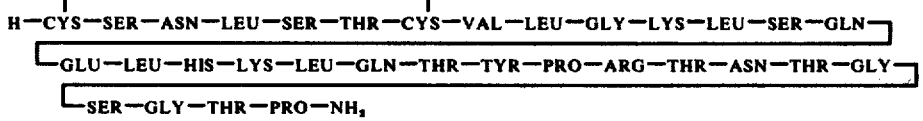

which is salmon calcitonin.

A specific example of the synthesis of salmon calcitonin using our improved process is given in Example I.

EXAMPLE I

Resin Activation

The BHA resin (5 g) with an amine titer of 0.61 meq/g was placed in the reactor vessel of a peptide synthesizer marketed by Schwarz-Mann, Inc. of Orangeburg, N.Y. The resin was treated with 25 ml of the following solvents filtering after each treatment.
Methylene Chloride — 2 minutes
Chloroform — 2 minutes two times each
10% triethylamine in chloroform — 5 minutes two times each
Chloroform — 2 minutes
Methylene Chloride — 2 minutes three times each

CYCLE 32

Coupling: The BHA resin, 25 ml of methylene chloride and 1.29 g (0.006 moles) or BOC-L-proline was stirred for 10 minutes. 6.0 ml of a methylene chloride solution of dicyclohexylcarbodiimide (1 milliequivalent of DCCI per 1 ml of solution) was added to the reactor and the mixture agitated for 6 hours. The reaction mixture was removed from the reactor by filtration and the BOC-prolyl BHA resin subjected to the following successive 2 minute, 25 ml washes, removing the wash by filtration each time:
Methylene chloride — two times
Methyl alcohol — two times
Methylene chloride — three times
Acetylation: The resin was then agitated with a mixture of 1.5 ml of triethylamine (TEA), 1 ml of acetic anhydride and 25 ml of chloroform for 2 hours. The reaction mixture was removed by filtration and the resin subjected to the following 2 minute, 25 ml washes:
Chloroform — two times
Methyl alcohol — two times
Methylene chloride — three times
Deprotection: The BOC-protected resin was agitated for 5 minutes with a mixture of 15 ml of trifluoroacetic acid (TFA) and 15 ml of methylene chloride. This mixture was removed by filtration and the resin was agitated with a second mixture of 15 ml of TFA and 15 ml of methylene chloride for 30 minutes. The reaction mixture was removed by filtration and the resin subjected to the following 25 ml washes:
Methylene chloride — two times two minutes each
Methyl alcohol — two times two minutes each
Chloroform — two times two minutes each 10% TFA in chloroform — two times ten minutes each
Chloroform — two times two minutes each
Methylene chloride — two times two minutes each.

The L-proline BHA resin was titrated to establish the amine or proline titer. This value was 0.55 milliequivalents of amine or proline per gram of resin.

CYCLE 31

Coupling: The L-prolyl resin, 25 ml of methylene chloride and 1.7 g (0.0055 mole) of BOC-O-benzyl-L-threonine were agitated for 10 minutes. Then 5.5 ml of a methylene chloride solution of dicyclohexylcarbodiimide (1 milliequivalent of DCCI per 1 ml of solution or a total of 0.0055 mole of DCCI) was added to the reactor and the mixture agitated for 2 hours. The reaction mixture was removed from the reactor and the resin was subjected to the following successive 2 minutes, 25 ml washes, removing the wash by filtration each time.
Methylene chloride — two times
Methyl alcohol — two times
Methylene chloride — three times
A ninhydrin test was negative.
Deprotection: The deprotection procedure described in Cycle 32 was repeated for this cycle.

CYCLES 30 through 27

The coupling and deprotection procedures used in these cycles were the same as in Cycle 31 except that the following amino acid derivatives were used in place of the threonine derivative:
Cycle 30 — 0.97 g. (0.0055 mole) of BOC-glycine
Cycle 29 — 1.62 g (0.0055 mole) of BOC-O-Benzyl-L-serine
Cycle 28 — The material used was the same as Cycle 30.
Cycle 27 — The material used was the same as Cycle 31.

CYCLE 26

Coupling: The peptide resin obtained from Cycle 27 was washed twice with 25 ml portions of dimethylformamide (DMF). The resin was then agitated for 24 hours with a solution of 2.9 g (0.008 mole) of BOC-L-asparagine p-nitrophenyl ester in 35 ml of DMF. The reaction mixture was filtered and the resin peptide subjected to two minute washes with two successive 25 ml portions of the following solvents: DMF, methylene chloride, methanol, methylene chloride. Each individual solvent was removed by filtration. A ninhydrin test was negative.
Deprotection: The deprotection procedure used in Cycle 32 was repeated.

CYCLE 25

Coupling and deprotection procedures were the same as Cycle 31 using the same materials and amounts.

CYCLE 24

Coupling: The resin peptide obtained from Cycle 25 was washed with two successive 25 ml portions of DMF. The resin peptide was then agitated for 10 minutes with a mixture of 3.43 g (0.008 mole) of BOC-N-tosyl-L-arginine and 25 ml of DMF. Then 8 ml of DCCI in methylene chloride (equivalent to 0.008 mole of DCCI) was added and the mixture agitated for 6 hours. The reaction mixture was removed by filtration. The resin peptide was subjected to two minute washes with two successive 25 ml portions of the following solvents: DMF, methylene chloride, methyl alcohol, methylene chloride. The ninhydrin test was negative.

Deprotection: Repeat deprotection procedures used in Cycle 32.

CYCLE 23

Coupling: The peptide resin obtained from Cycle 24 was agitated for 10 minutes with 1.77 g (0.008 mole) of BOC-L-proline and 25 ml of methylene chloride. 8 ml of DCCI in methylene chloride (equivalent to 0.008 mole of DCCI) was added and the mixture agitated for 6 hours. The reaction mixture was removed by filtration and the resin peptide subjected to two minute washes with two successive 25 ml portions of the following solvents: methylene chloride, methyl alcohol, methylene chloride. Each individual solvent was removed by filtration. The ninhydrin test was negative.

Deprotection: The deprotection procedure used in Cycle 32 was repeated.

CYCLES 22 and 21

The coupling and deprotection procedures used in these cycles were the same as in Cycle 24 except that in the coupling reaction the following amino acid derivatives were used in place of BOC-L-proline.

Cycle 22 — 2.97 g (0.008 mole) of BOC-O-benzyl-L-tyrosine
Cycle 21 — 2.74 g (0.008 mole) of BOC-O-benzyl-L-threonine

CYCLE 20

This procedure is the same as Cycle 26 except that 3.0 g (0.008 mole) of BOC-L-glutamine p-nitrophenyl ester is used in place of the asparagine derivative.

CYCLES 19 through 15

The procedure is the same as used in Cycle 31 except that the following amino acid derivatives were used in place of the threonine derivative:
Cycle 19 — 1.37 g (0.0055 mole) of BOC-L-leucine
Cycle 18 — 2.09 g (0.0055 mole) of BOC-ε-carbobenzyloxy-L-lysine
Cycle 17 — 2.58 g (0.0055 mole) of BOC-N(im)carbobenzyloxy-L-histidine
Cycle 16 — See Cycle 19
Cycle 15 — 1.85 g (0.0055 mole) of BOC-L-glutamic acid γ-benzyl ester

CYCLE 14

Same as Cycle 20.

CYCLE 13

The procedure used was the same as used in Cycle 23 except that in the coupling reaction 2.36 g (0.008 mole) of BOC-O-benzyl-L-serine was used in place of the proline derivative.

CYCLES 12 through 9

The procedures used were the same as used in Cycle 31 except in the coupling reactions the following amino acid derivatives were used in place of the threonine derivative.

Cycle 12 — Same material as used in Cycle 19
Cycle 11 — The material used was the same as in Cycle 18
Cycle 10 — Same material as used in Cycle 30
Cycle 9 — Same material as used in Cycle 19

CYCLE 8

Coupling: The resin peptide from Cycle 9 was agitated for 10 minutes with 1.79 g (0.008 mole) of BOC-L-valine and 25 ml of methylene chloride. Then 8 ml of DCCI in methylene chloride (equivalent to 0.008 mole of DCCI) was added and the mixture agitated for 16 hours. The reaction mixture was removed by filtration. The resin peptide was subjected to two minute washes with two successive 25 ml portions of the following solvents: methylene chloride, methyl alcohol, methylene chloride. Each individual was was removed by filtration.

Deprotection: See Cycle 22.

CYCLE 7

The procedure was the same as used in Cycle 31 except that in the coupling reaction 1.88 g (0.0055 mole) BOC-S-p-methoxybenzyl-L-cysteine was used in place of the threonine derivative.

CYCLE 6

The materials and procedures used were the same as Cycle 31.

CYCLE 5

The materials and procedures used were the same as Cycle 29.

CYCLE 4

The materials and procedures used were the same as Cycle 19.

CYCLE 3

The materials and procedures used were the same as Cycle 26.

CYCLE 2

The materials and procedures used were the same as Cycle 29.

CYCLE 1

The resin peptide obtained from Cycle 2 was washed with two successive 20 ml portions of DMF. The resin peptide was then agitated for 10 minutes with a mixture of 2.4 g (0.0055 mole) of bis-BOC-L-cystine and 20 ml of DMF. Then 11.0 ml of methylene chloride solution of dicyclohexylcarbodiimide (1 meq of DCCI per ml of solution or a total of 0.011 mole of DCCI) was added to the reactor and the mixture agitated for 2 hours. The reaction mixture was removed from the reactor and the resin peptide was subjected to the following successive 2 minute, 20 ml washes, removing the wash by filtration each time.
DMF — two times
Methylene chloride — two times
Methyl alcohol — two times
Methylene chloride — two times
A ninhydrin test was negative.

Deprotection: Repeat the deprotection procedure used in Cycle 31.

After completion of Cycle 1 the resin peptide was washed with two successive 25 ml portions of n-hexane. The peptide material was removed from the reactor and dried in an electric vacuum oven at 40° C and 0.1 mm of Hg for 24 hours.

Cleavage with Hydrogen Fluoride

The dried resin peptide (16 g) and 16 ml of anisole were placed in a Teflon reaction vessel. The vessel equipped with a Teflon-coated magnetic stirrer was placed in a dry ice-acetone bath and 100 ml of hydrogen fluoride gas was condensed into the vessel. This mixture was stirred at 0° C. in an ice bath for 1 hour. The hydrogen fluoride was removed by evaporation at reduced pressure. The residue was triturated with six 100 ml portions of ethyl acetate. The peptide was extracted from the resin beads with 800 ml of 0.1 molar aqueous acetic solution.

Cyclization of Peptide to Salmon Calcitonin

The aqueous acetic acid extract obtained from hydrogen fluoride cleavage was diluted to 1.5 liters by addition of 700 ml of distilled water. The pH of the solution was adjusted to 7.5 by the addition of concentrated ammonium hydroxide. The solution was stirred in a closed vessel under a stream of nitrogen for 12 hours. The pH of the reaction mixture was adjusted to 5.0 by addition of glacial acetic acid.

Purification of the Crude Salmon Calcitonin

The 1.5 liters of solution from the above synthesis at pH 5.0 was concentrated using a SP-Sephadex C-25 ion-exchange column. The 75 ml concentrate removed from the column with 0.5 molar sodium chloride solution was desalted and purified by passing through a Sephadex G-25 (fine) gel-filtration column and eluting with 0.03 molar aqueous acetic acid solution. The salmon calcitonin fraction from this column was adjusted to pH 6.0 by addition of ammonium hydroxide solution. This solution was further purified by ion-exchange chromatography using a Whatman CM52 column eluted with ammonium acetate buffer. The salmon calcitonin fraction from this column was adjusted to pH 5.0 by addition of glacial acetic acid. This solution was concentrated using a SP-Sephadex C-25 ion-exchange column. The 30 ml concentrate removed from the column with 0.5 molar sodium chloride solution was desalted with a Sephadex G-25 (fine) gel-filtration column. The purified salmon clacitonin fraction was collected and freeze-dried. The product was obtained as a fluffy white solid. This material was found to be biologically and chemically equivalent to the product reported in literature (Guttman, S., et., Helv. Chim. Acta 52, 1789–1795 [1969]).

The preparation of the compounds as heretofore described or as set forth in Example I may be varied in many respects, but when variations in more than one factor are made it is difficult to evaluate any one of the changed factors. For this reason, we set up a series of tests in which only one factor is varied and the results compared.

Another application of our improved process is in the synthesis of oxytocin. Oxytocin includes nine amino acids, and the amino acid chain for oxytocin may be built beginning with glycine at position 9. The glycine may be coupled to the BHA resin using the reactant BOC-glycine; then leucine may be coupled using the reactant BOC-L-leucine, and then following through using cycles of coupling and deprotection according to the solid phase technique, using in sequence the specified amino acid groups and protective groups as set forth in Table II.

When position No. 6 is reached, an acid labile protected cysteine derivative is used, and when position No. 1 is reached, bis-BOC- cystine is coupled to the amino terminal end of the peptide.

The peptide after completion of the amino acid chain may be written:

$$\begin{array}{c} \text{H—CYS} \quad \text{W} \\ | \quad\quad | \\ \text{H—CYS—TYR—ILE—GLN—ASN—} \end{array}$$

$$\begin{array}{c} \text{P} \\ | \\ \text{—CYS—PRO—LEU—GLY—NHCH— X} \\ | \\ \text{C}_6\text{H}_5 \end{array}$$

where
- X is the polystyrene portion of the resin
- W is no protective group, a BZ group, or benzyloxycarbonyl group or a benzyloxycarbonyl derivative group and
- is a tertiary or secondary alkylthio group or a benzyl or benzyl derivative group.

After the acid treatment to cleave the resin then becomes:

$$\begin{array}{c} \text{H—CYS} \\ | \\ \text{H—CYS—TYR—ILE—GLN—ASN—} \end{array}$$

$$\text{—CYS—PRO—LEU—GLY—NH}_2.$$

This cleaved peptide retaining the cystine residue at the amino terminal end position, when held in a solvent, preferably at pH 6.0 to 8.5, undergoes rearrangement of the disulfide bond between the free cysteine and the cystine residue at the amino terminal end to yield the peptide written as follows:

$$\begin{array}{c} \overline{\phantom{XXXXXXXXXXXXXXXXXXXXXX}} \\ \text{H—CYS—TYR—ILE—GLN—ASN—CYS—} \end{array}$$

$$\text{—PRO—LEU—GLY—NH}_2$$

which is oxytocin.

A specific example of the synthesis of oxytocin using our improved process is given in the following Example II.

EXAMPLE II

SYNTHESIS OF OXYTOCIN

RESIN ACTIVATION

The benzhydrylamine (BHA) resin (5 g) with an amine titer of 0.43 meq/g was placed in the reaction vessel of a peptide synthesizer marketed by Schwartz-Mann, Inc. of Orangeburg, New York. The resin was treated with 20 ml of the following solvents filtering after each treatment:

Methylene chloride —two minutes
Chloroform —two minutes two times each
10 % Triethylamine in chloroform —five minutes two times each
Choloroform —two minutes
Methylene chloride —two minutes three times each.

CYCLE 9

Coupling: The BHA resin, 20 ml of methylene chloride and 0.75 g (0.0043 mole) of BOC-glycine were agitated for 10 minutes. 4.3 ml of a methylene chloride solution of dicyclohexylcarbodiimide (1 meq of DCCI per 1 ml of solution) was added to the reactor and the mixture agitated for 6 hours. The reaction mixture was removed from the reactor by filtration and the BOC-glycyl BHA resin subjected to the following successive 2 minute, 20 ml washes, removing the wash by filtration each time:
- Methylene chloride —two times
- Methyl alcohol —two times
- Methylene chloride —two times Acetylation: The resin was then agitated with a mixture of 1.6 ml of acetic anhydride, 2.4 ml of triethylamine (TFA) and 20 ml of chloroform for 30 minutes. The reaction mixture was removed by filtration and the resin subjected to the following 2 minute, 20 ml washes:
- Chloroform —two times
- Methyl alcohol —two times
- Methylene chloride —three times A negative test was found for a ninhydrin assay.

Deprotection: The BOC-protected resin was agitated for 5 minutes with a mixture of 12 ml of trifluoroacetic acid (TFA) and 12 ml of methylene chloride. The mixture was removed by filtration and the resin was agitated with a second mixture of 12 ml of TFA and 12 ml of methylene chloride for 30 minutes. The reaction mixture was removed by filtration and the resin subjected to the following 20 washes:
- Methylene chloride —2 times two minutes each
- Methyl alcohol —2 times two minutes each
- Chloroform —2 times two minutes each
- 10 % TEA in chloroform —2 times five and ten minutes
- Chloroform —2 times two minutes each
- Methylene chloride —2 times two minutes each The L-glycine BHA resin was titrated (Dorman, L., Tetrahedron Letters, 1969, 2319-21 ) to establish the amine or glycine titer. This value was 0.384 meq of amine or glycine per gram of resin.

CYCLE 8

Coupling: The L-glycine resin, 20 ml of methylene chloride and 2.95 g (0.0038 mole) of BOC-L-leucine $H_2$ O were agitated for 10 minutes. Then 3.8 ml of methylene chloride solution of dicyclohexylcarbodiimide (1 meq of DCCI per 1 ml of solution or a total of 0.038 mole of DCCI) was added to the reactor and the mixture agitated for 2 hours. The reaction mixture was removed from the reactor and the resin was subjected to the following successive 2 minute, 20 ml washes, removing the wash by filtration each time:
- Methylene chloride —two times
- Methyl alcohol —two times
- Methylene chloride —two times A ninhydrin test was negative.

Deprotection- The deprotection procedure described in Cycle 9 was repeated for this cycle.

CYCLE 7

The coupling and deprotection procedures used in this cycle were the same as in Cycle 8 except that the following amino acid derivative was used in place of the leucine derivative:

0.82 g (0.0038 mole) of BOC-L-proline

CYCLE 6

The coupling and deprotection procedures used in this cycle were the same as in Cycle 8. The acetylation procedure was performed in this cycle using the same method as in Cycle 9. The following amino acid derivative was used in the coupling procedure:

1.3 g. (0.0038 mole) of BOC-S-3,4 -dimethylbenzyl-L-cystenine

CYCLE 5

Coupling: The peptide resin obtained from Cycle 6 was washed twice with 20 ml portions of dimethylformamide (DMF). The resin was then agitated for 24 hours with a solution of 2.01 g (0.0057 mole) of BOC-L-asparagine-p-nitrophenyl ester in 25 ml of DMF. The reaction mixture was filtered and the resin peptide subjected to two minute washes with two successive 20 ml portions of the following solvents: DMF, methylene chloride, methanol, methylene chloride. Individual solvent washes were removed by filtration. A ninhydrin test was negative.

Deprotection: The deprotection procedure used in Cycle 8 was repeated.

CYCLE 4

The coupling procedure used in this cycle was the same as in Cycle 5. The acetylation procedure was performed in this cycle using the same method as in Cycle 9 . The deprotection procedure used in this cycle was the same as in Cycle 8. The following amino acid derivative was used;

2.09 g (b 0.0057 mole) of BOC-L-glutamine-p-nitrophenyl ester

CYCLE 3

The coupling procedure used in this cycle was the same as in Cycle 8. The coupling was repeated using a solvent system of DMF 10 ml and methylene chloride 10 ml and the same amounts of amino acid and DCC. The acetylation procedure used in this cycle was the same as in Cycle 9. The deprotection procedure used in this cycle was the same as in Cycle 8. The following amino acid derivative was used for each coupling reaction:

0.88 g (0.0038 mole) of BOC-L-isoleucine

CYCLE 2

Coupling: The resin peptide obtained from Cycle 3 was washed with two successive 20 ml portions of DMF. The resin peptide was then agitated for 10 minutes with a mixture of 2.11 g (0.0057 mole) of BOC-O-benzyl-L-tyrosine and 20 ml of DMF. Then 5.7 ml of DCCI in methylene chloride (equivalent to 0.0057 mole of DCCI) was added and the mixture agitated for 16 hours. The reaction mixture was removed by filtration. The resin peptide was subjected to two minute washes with two successive 20 ml portions of the following solvents: DMF, methylene chloride, methanol, methylene chloride.

The coupling was repeated using half the amounts of the amino acid derivative and DCCI in methylene chloride for an agitation time of 6 hours.

Acetylation: Repeat acetylation procedure used in Cycle 9 .

Deprotection: Repeat deprotection procedure used in Cycle 9 .

CYCLE 1

The resin peptide obtained from Cycle 2 was washed with two successive 20 ml portions of DMF. The resin peptide was then agitated for 10 minutes with a mixture of 1.7 g (0.0038 mole) of bis-BOC-L-cystine and 20 ml DMF. Then 7.6 ml of methylene chloride solution of dicyclohexylcarbodiimide (1 meq of DCCI per ml. of solution or a total of 0.0076 mole of DCCI) was added to the reactor and the mixture agiated for 2 hours. The reaction mixture was removed form the reactor and the resin peptide was subjected to the following successive 2 minute, 20 ml washes, removing the wash by filtration each time:
DMF — two times
Methylene chloride — two times
Methyl alcohol — two times
Methylene chloride — two times
A ninhydrin test was negative.

Deprotection; Repeat the deprotection procedure used in Cycle 9 .

The peptide material was removed from the reactor by rinsing with hexane and dried in an electric vacuum over at 40° C. and 0.1 mm of Hg for 24 hours. The blocked oxytocin peptide resin weighed 6.8 g.

Cleavage with Hydrogen Fluoride

The dried resin peptide (2 g) and 2 ml of anisole were placed in a Teflon reaction vessel. The vessel equipped with a Teflon-coated magnetic stirrer was placed in a dry ice-acetone bath and 15 ml of hydrogen fluoride gas was condensed into the vessel. This mixture was stirred at 0° C. in an ice bath for one hour. The residue was triturated with 4 × 25 ml portions of ethyl acetate. The peptide was extracted from the resin beads with 2 = 50 ml portions of glacial acetic acid. The extract was lyophilized to the cleaved peptide.

Cyclization of Peptide to Oxytocin

The crude peptide, 200 mg, was partially dissolved in 50 of oxygen-free distilled water with 1 ml of glacial acetic acid added. The pH of the solution was adjusted to 7.5 by the addition of concentrated ammonium hydroxide. This mixture was stirred in a closed vessel under a stream of nitrogen for 24 hours. The reaction mixture was adjusted to pH of 3.2 by addition of glacial acetic acid. It was lyophilized to give a solid residue.

Purification of the Crude Oxytocin

This solid residue was dissolved in 0.5 N acetic acid solution and purified by passing through a Sephadex G-25 (fine) gel-filtration column and eluted with 0.5 N acetic acid. The oxytocin fraction from this column was collected and lyophilized to give a white solid.

This solid was again dissolved in 0.5 N acetic acid solution and purified by passing through the Sephadex G-25 (fine) gel-filtration column and eluted with 0.5 N acetic acid solution and purified by passing through the Sephadex G-25 (fine) gel-filtration column and eluted with 0.5 N acetic acid solution. The oxytocin fraction from this column was collected and lyophilized to give a fluffy white solid. This product was assayed and the following amino acid ratios found: GLY 1.0, LEU 0.98, PRO 0.97, ASP 0.89, GLU 0.84, ILE 0.74, TYR 0.72. The theoretical amount should be 1.0. The value for CYS was not reported because the assay method destroys this amino acid. The biological potency of the product was 305.4 units per mg.

Our improved process may be applied to the synthesis of human calcitonin in a similar manner to that described in connection with salmon calcitonin. Human calcitonin includes 32 amino acids in its amino acid chain. Starting with proline, this amino acid at position =is coupled with a BHA resin, then alanine at position 31, is and glycine at position 30 are attached according to the system of protection, coupling and deprotection previously explained, using the reactants, including amino acid groups and protecting groups, as are set forth in Table IV in the sequence indicated. When the cysteine group is reached at position 7, an acid labile protected cysteine derivative is used. When position 1 is reached, bis-BOC-L-cystine is used as the cysteine derivative.

When the amino acid chain is completed, the peptide may be written:

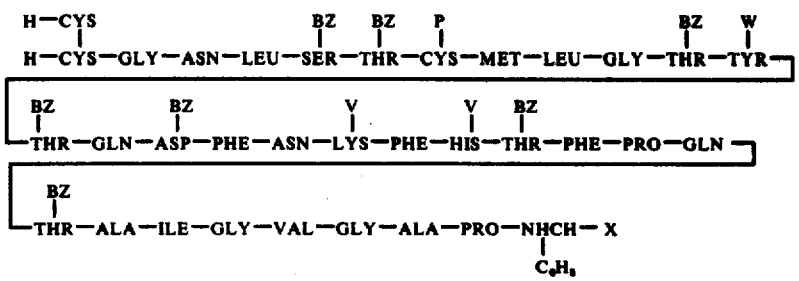

After treatment with acid to remove the resin and acid labile groups, the peptide becomes:

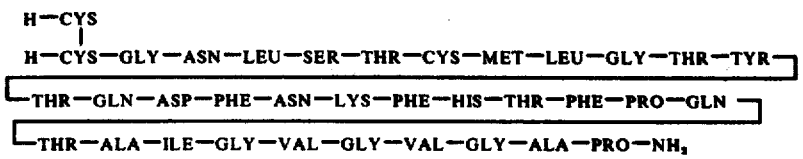

After this peptide has been allowed to rearrange under conditions as described herein for completing the disulfide ring, it may be written:

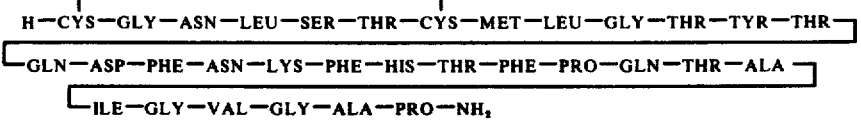

which is the structure of human calcitonin.

A specific example of the synthesis of human calcitonin using our improved process is given in Example III.

EXAMPLE III

Synthesis of Human Calcitonin

Resin Activation

The benzhydrylamine (BHA) resin (4 g) with an amine titer of 0.55 meq/g was placed in the reactor vessel of a peptide synthesizer marketed by Schwartz-Mann, Inc. of Orangeburg, N.Y. The resin was treated with 20 ml of the following solvents filtering after each treatment:

Methylene Chloride — two minutes
Chloroform — two minutes two times each
10% Triethylamine in chloroform — five minutes two times each
Chloroform — two minutes
Methylene chloride — two minutes three times each.

CYCLE 32

Coupling: The BHA resin, 20 ml of methylene chloride and 0.95 (0.0044 mole) of BOC-L-proline were agitated for 10 minutes. 4.4 ml of a methylene chloride solution of dicyclohexylcarbodiimide (1 milliequivalent of DCCI per 1 ml of solution) was added to the reactor and the mixture agitated for 6 hours. The reaction mixture was removed from the reactor by filtration and the BOC-prolyl BHA resin subjected to the following successive 2 minute, 20 ml washes, removing the wash by filtration each time:

Methylene chloride — two times
Methyl alcohol — two times
Methylene chloride — two times Acetylation: The resin was then agitated with a mixture of 1.5 ml of triethylamine (TEA), 1 ml of acetic anhydride and 20 ml of chloroform for two hours. The reaction mixture was removed by filtration and the resin subjected to the following 2 minute, 20 ml washes;

Chloroform — two times
Methyl alcohol — two times
Methylene chloride — three times A ninhydrin test was negative (E. Kaiser, et al., Anal. Biochem., 34, 595-8 [1970].

Deprotection: The BOC-protected resin was agitated for 5 minutes with a mixture of 12.5 ml of trifluoroacetic acid (TFA) and 12.5 ml of methylene chloride. This mixture was removed by filtration and the resin was agitated with a second mixture of 12.5 ml of TFA and 12.5 ml of methylene chloride for 30 minutes. The reaction mixture was removed by filtration and the resin subjected to the following 20 ml washes:

Methylene chloride — 2 times two minutes each
Methyl alcohol — 2 times two minutes each
Chloroform — 2 times two minutes each
10% TEA in chloroform — 2 times ten minutes each
Chloroform — 2 times two minutes each
Methylene chloride — 2 times two minutes each The L-proline BHA resin was titrated to establish the amino or proline titer. This value was 0.494 milliequivalents of amine or proline per gram of resin.

CYCLE 31

Coupling: The L-prolyl resin, 20 ml of methylene chloride and 0.83 g (0.0044 mole) of BOC-alanine were agitated for 10 minutes. The 4.4 ml of a methylene chloride solution of dicyclohexycarbodiimide (1 milliequivalent of DDCI per 1 ml of solution or a total of 0.0044 mole of DDCI) was added to the reactor and the mixture agitated for 2 hours. The reaction mixture was removed from the reactor by filtration and the BOC-L-alanyl-L-prolyl BHA resin subjected to the following successive 2 minute, 20 ml washes, removing the wash by filtration each time:

Methylene chloride — two times
Methy alcohol — two times
Methylene chloride — three times A ninhydrin test was negative.

CYCLES 30 Through 26

The coupling and deprotection procedures used in these cycles were the same as in Cycle 31 except that the following amino acid derivatives were used in place of the alanine derivative:

Cycle 30 — 0.77 g (0.0044 mole) of BOC-glycine
Cycle 29 — 0.95 g (0.0044 mole) of BOC-L-valine
Cycle 28 — The material used was the same as Cycle 30
Cycle 27 — 1.02 g (0.0044 mole) of BOC-L-isoleucine
Cycle 26 — The material used was the same as Cycle 31

CYCLE 25

Coupling: The peptide resin obtained from Cycle 26 was washed twice with 20 ml portions of dimethylformamide (DMF). The resin peptide was then agitated for 10 minutes with a mixture of 2.04 g (0.0066 mole) of BOC-O-benzyl-L threonine and 20 ml of DMF. The 6.6 ml of DCCI in methylene chloride (equivalent to 0.0066 mole of DCCI) was added and the mixture agitated for 6 hours. The reaction mixture was removed by filtration. The resin peptide was subjected to two minute washes with two successive 20 ml portions of the following solvents: DMF, methylene chloride, methyl alcohol, methylene chloride. The ninhydrin test was negative.

Deprotection: Repeat deprotection procedure used in Cycle 32.

CYCLE 24

Coupling: The peptide resin obtained from Cycle 25 was washed twice with 20 ml portions of DMF. The resin was then agitated for 24 hours with a solution of 2.42 g (0.0066 mole) of BOC-L-glutamine-p-nitrophenyl ester in 25 ml of DMF. The reaction mixture was filtered and the resin peptide subjected to two minute washes with two successive 20 ml portions of the following solvents: DMF, methylene chloride, methanol, methylene chloride. Each individual solvent was removed by filtration. A ninhydrin test was negative.

Deprotection: The deprotection procedure used in Cycle 32 was repeated.

CYCLE 23

Coupling: The peptide resin obtained from Cycle 24 was agitated for 10 minutes with 1.42 g (0.0066 mole) of BOC-L-proline and 20 ml of methylene chloride. 6.6 ml of DCCI in methylene chloride (equivalent to 0.0066 mole of DCCI) was added and the mixture agitated for 16 hours. The reaction mixture was removed by filtration and the resin peptide was subjected to two minute washes with two successive 20 ml portions of the following solvents: methylene chloride, methyl alcohol, methylene chloride. Each individual wash was removed by filtration. The ninhydrin test was negative.

Deprotection: The deprotection procedure used in Cycle 32 was repeated.

CYCLE 22

The coupling and deprotection procedure used in this cycle were the same as in Cycle 23 except that in the coupling reaction, 1.75 g. (0.0066 mole) of BOC-L-phenylalanine was used in place of BOC-L-proline.

CYCLES 21 through 18

The coupling and deprotection procedures used in these cycles were the same as in Cycle 31 except that the following amino acid derivatives were used in place of the alanine derivative:
Cycle 21 — 1.36 g (0.0044 mole) of BOC-O-benzyl-L-threonine
Cycle 20 — 1.71 g (0.0044 mole) of BOC-N (im)-carbobenzyloxy-L-histidine
Cycle 19 — 1.17 g (0.0044 mole) pf BDC-L-phenylalanine
Cycle 18 — 1.67 g (0.0044 mole) of BOC- ε-carbobenzyloxy-Llysine

CYCLE 17

The coupling and deprotection procedure used in this cycle were the same as in Cycle 24 except that 2.33 g (0.0066 mole) of BOC-L-asparagine-p-nitrophenyl ester was used in place of the glutamine derivative.

CYCLES 16 and 15

The coupling and deprotection procedures used in these cycles were the same as in Cycle 31 except that the following amino acid derivatives were used in place of the alanine derivative:
Cycle 16 — 1.17 g (0.0044 mole) of BOC-L-phenylalanine
Cycle 15 — 1.42 g (0.0044 mole) of BOC-L-aspartic acid-β-Benzyl ester

CYCLE 14

Same as cycle 24.

CYCLE 13

Same as Cycle 21.

CYCLE 12

The coupling and deprotection procedures used in this cycle were the same as in Cycle 25 except that 2.45 g (0.0066 mole) of BOC-O-benzyl-L-tyrosine was used in place of the threonine derivative and the agitation time was extended to 16 hours.

CYCLE 11

Same as Cycle 25

CYCLES 10 through 7

The coupling and deprotection procedures used in these cycles were the same as in Cycle 31 except that in the coupling reaction the following amino derivatives were used in place of the BOC-L-alanin.
Cycle 10 — 0.77 g (0.0044 mole) of BOC-glycine
Cycle 9 — 1.02 g (0.0044 mole) of BOC-L-leucined
Cycle 8 — 1.1 g (0.0044 mole) of BOC-L-methionine
Cycle 7 — 1.5 g (0.0044 mole) of BOC-S-3,4 dimethylbenzyl-L-cysteine

CYCLE 6 Same as Cycle 25.

CYCLES 5 and 4

The coupling and deprotection procedures used in these cycles were the same as in Cycle 31 except that in the coupling reaction the following amine derivatives were used in place of the BOC-L-alanine:
Cycle 5 — 1.3 g (0.0044 mole) of BOC-O-benzyl-L-serine
Cycle 4 — 1.02 g (0.0044 mole) of BOC-L-leucine

CYCLE 3

Same as Cycle 17. CYCLE Lb 2

The coupling and deprotection procedures used in Cycle 2 were the same as in cycle 31 except that in the coupling reaction of the following amino acid derivative was used in place of the BOC-L-alanine:
0.77 g (0.0044 mole) of BOC-glycine

CYCLE 1

Coupling: The resin peptide from Cycle 2 was washed with two successive 20 ml portions of DMF. The resin peptide was then agitated for 10 minutes with a mixture of 1.9 g (0.0044 mole) of bis-BOC-L-cystine and 20 ml of DMF. Then 8.8 ml of methylene chloride solution of dicyclohexylcarbodiimide (1 meq of DCCI per ml of solution or a total of 0.0088 mole of DCCI) was added to the reactor and the mixture agitated for 2 hours. The reaction mixture was removed from the reactor and the resin peptide was subjected to the following successive 2 minute, 20 ml washes, removing the wash by filtration each time:
DMF — two times
Methylene chloride — two times
Methyl alcohol — two times
Methylene chloride — two times
A ninhydrin test was negative.

Deprotection: Repeat the deprotection procedure used in Cycle 31.

After completion of Cycle 1, the resin peptide was washed with two successive 20 ml portions of n-hexane. The peptide material was removed from the reactor and dried in an electric vacuum oven at 40° C. and 0.1 mm of Hg for 24 hours. The blocked human calcitonin peptide resin weighed 10.3 g.

Cleavage with Hydrogen Fluoride

The dried resin peptide (2 g) and 2 ml of anisole were placed in a Teflon reaction vessel. The vessel equipped with a Teflon-coated magnetic stirrer was placed in a dry-ice bath and 15 ml of hydrogen fluoride gas was condensed into the vessel. This mixture was stirred at 0° C. in an ice bath for 1 hour. The hydrogen fluoride was removed by evaporation at reduced pressure. The residue was triturated with 2 × 25 ml portions of ethyl acetate. The peptide was extracted from the resin beads with 2 × 50 ml of glacial acetic acid. The extract was lyophilized to give the cleaved peptide.

Cyclization of Peptide to Human Calcitonin

The crude peptide 1000 mg was dissolved in 250 ml of oxygen-free distilled water with 1 ml of glacial acetic acid added. The pH of the solution was adjusted to 7.5 by the additional concentrated ammonium hydroxide. This mixture was stirred in a closed vessel under a stream of nitrogen for 24 hours. The pH of the reaction mixture was adjusted to 3.2 by the addition of glacial acetic acid. Lyophilization gave a solid product.

Purification of the Crude Human Calcitonin

The solid product was dissolved in 0.5 N acetic acid and purified by passing through a Sephadex G-25 (fine) gel-filtration column and eluted with 0.5 N acetic acid. The human calcitonin fraction from this column was collected and lyophilized to give a white fluffy solid.

This white fluffy solid was dissolved in 0.05 M aqueous ammonium acetate (pH 5). The solution was adjusted to pH 5 and purified by ion-exchange chromatography using a SP-Sephadex C-25 column eluted with ammonium acetate buffer. The human calcitonin fraction was collected and lyophilized twice to give a fluffy white solid. This material was found to be biologicaly and chemically equivalent to the product reported in the literature (Sieber, P., et al., Helv. Chim. Acts, 53, 2135—50 (1970). The amino acid analysis (acid hydrolysis) gave the following ratios of amino acids (the theoretical result is given in parenthesis): LYS 1.03 (1), HIS 0.99 (1), ASP 3.18 (3), THR 5.11 (5), SER 0.84 (1), GLU 1.95 (2), GLY 4.31 (4), ALA 2.03 (2), VAL 0.95 (1), MET 0.90 (1), ILE 1.04 (1), LEU 2.24 (2), TYR 0.8 (1), PHE 3.0 (3). The values for PRO and CYS were not determined. The biological activity was found to be 110 MRD units per mg.

Likewise, our improved process may be applied in the synthesis of vasopressin using as the reactants in the amino acid chain the groups set forth in Table V or equivalent thereof. The formula of the peptide resulting from the reactions referred to in Table V and before cleavage of the resin, may be written:

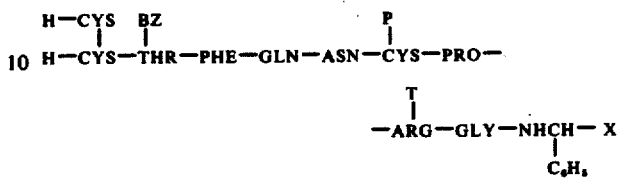

After acid treatment of this peptide to cleave the resin and most of the protective groups, the formula becomes:

which is a precursor of vasopressin.

After subjecting this peptide to our improved cyclizing method as herein described, the peptide becomes:

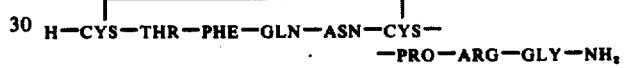

which is vasopressin.

To apply the improved process in the synthesis of porcine calcitonin, the amino acid chain for porcine calcitonin may be built using the reactants set forth in Table VI or equivalents thereof. The formula of the peptide resulting from the reactions illustrated in Table VI, and before cleavage of the resin, may be written:

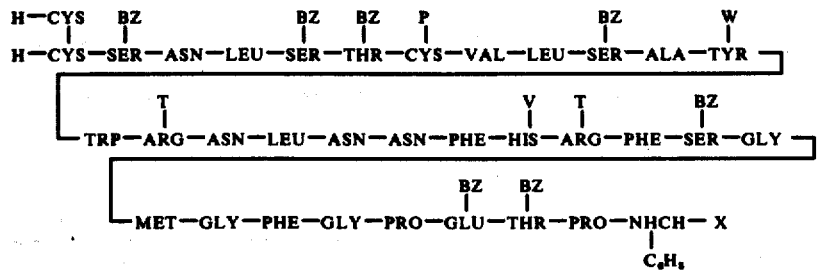

After acid treatment to cleave all acid labile protecting groups, the formula becomes:

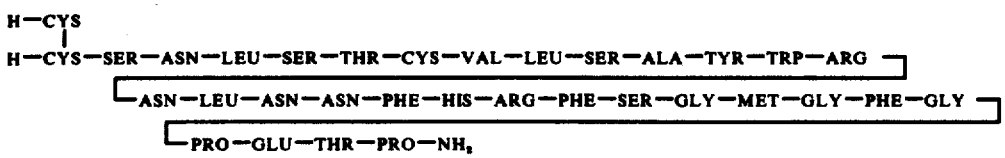

which is a precursor of porcine calcitonin.

After subjecting this peptide to our improved cyclizing method as herein described, the peptide becomes:

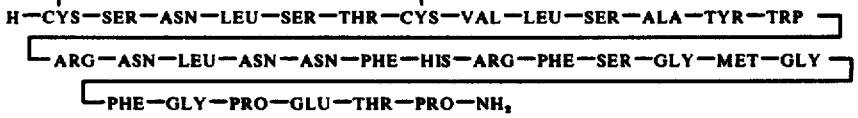

which is porcine calcitonin.

To apply the improved process in the synthesis of bovine calcitonin, the amino acid chain for bovine calcitonin may be built using the reactants set forth in Table VII or equivalents thereof. The formula fo the peptide resulting from the reactions illustrated in Table VII and before cleavage of the resin, may be written:

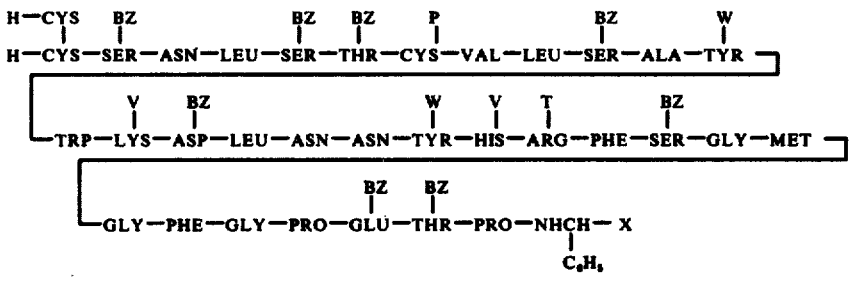

After acid treatment of this peptide to cleave the resin and most of the protective groups, the formula becomes:

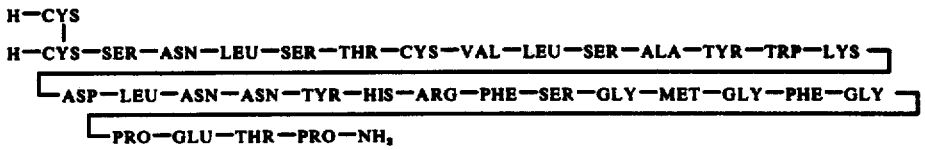

which is a precursor of bovine calcitonin.

After subjecting this peptide to our improved cyclizing method as herein described, the peptide becomes:

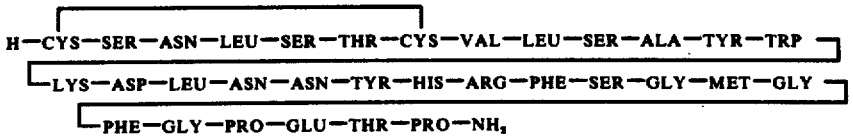

which is bovine calcitonon.

While the invention has been specifically described and deomonstrated with respect to specific peptides, it will be apparent to those skilled in this art that the invention is applicable to numerous specific peptide structures, and that the invention may be varied and changed in many ways all within the spirit of the invention and within the scope of the appended claims.

What is claimed is:

1. In a process for preparing a peptide having a disulfide ring structure, the step of holding a peptide which contains an amino terminal cystine residue and a cysteine residue located in a position within the amino acid sequence in a solution substantially free of oxygen until rearrangement has taken place to yield a cyclic disulfide peptide.

2. A process as set forth in claim 1 in which said solution is an aqueous solution.

3. A process as set forth in claim 1 in which said solution is an aqueous alcoholic solution.

4. A process as set forth in claim 2 which includes the step of agitating said soluting during said rearrangement.

5. A process as set forth in claim 1 including conducting said rearrangement under a stream of inert gas.

6. a process as set forth in claim 5 wherein said gas is nitrogen.

7. A process as set forth in claim 5 which includes continuing the process for a period of at least one hour.

8. A process as set forth in clain 1 in which said peptide is:

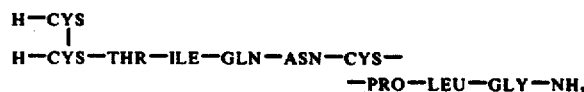

9. a process as set forth in claim 1 in which said peptide is:

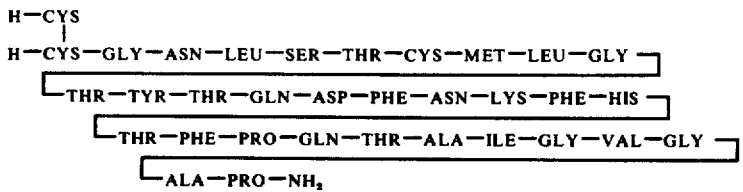

10. A process as set forth in claim 1 in which said peptide is:

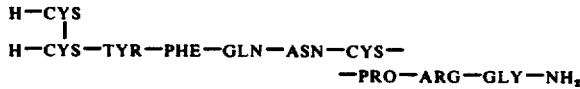

11. A process as set forth in claim 1 which includes the preparation of said peptide by coupling said cysteine residue into an amino acid chain while protecting the sulfhydryl function of said residue with a group selected from the class consisting of benzyl, 4-methoxybenzyl, 4-methylbenzyl, 3,4-dimethylbenzyl, 4-chlorobenzyl, 2,6-dichlorobenzyl, 4-nitrobenzyl, benzylhydryl, tertiary butylthio and isopropylthio, and coupling cystine residue into said chain at its amino terminal end, and treating the peptide so formed with anhydrous acid to cleave said selected group from said cysteine residue.

12. A process as set forth in claim 11 in which said chain includes the following sequence of amino acid moieties:

13. A process as set forth in claim 11 in which said chain includes the following sequence of amino acid moieties:

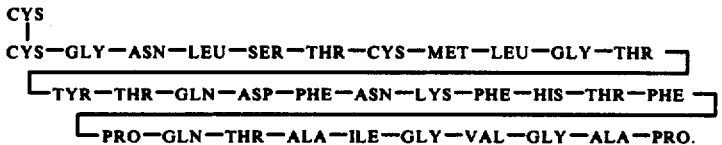

14. A peptide having an amino acid sequence the same as that of a natural calcitonin and which contains an amino terminal cystine moiety and a cysteine moiety within said sequence having a free sulfhydryl function.

15. A peptide as set forth in claim 14 in which said amino acid sequence is the same as in salmon calcitonin except that the amino terminal moiety is cystine.

16. A peptide having an amino acid sequence which is the same as that of oxytocin and containing an amino terminal cystine moiety and a cysteine moiety within said sequence having a free sulfhydryl function.

17. a peptide having an amino acid sequence the same as that of vasopressin and containing an amino terminal cystine moiety and a cysteine moiety within said sequence having a free sulfhydryl function.

18. A peptide as set forth in claim 14 in which said amino acid sequence is the same as in human calcitonin except that the amino terminal moiety is cystine.

19. A peptide as set forth in claim 14 in which said amino acid sequence is the same as in procine calcitonin except that the amino terminal moiety is cystine.

20. A peptide as set forth in claim 14 in which said amino acid sequence is the same as in bovine calcitonin except that the amino terminal moiety is cystine.

21. A peptide having an amino acid sequence the same as that of a natural calcitonin and which contains an amino terminal cystine moiety and an intermediate cysteine moiety having its sulfhydryl function protected by a group selected from the class consisting of benzyl, 4-methoxybezyl, 4-methylbenzyl, 3,4-dimethylbenzyl, 4-chlorobenzyl, 2,6-dichlorobenzyl, 4-nitrobenzyl, benzylhydryl, tertiary butylthio, and isopropylthio.

* * * * *